US011020554B2

(12) United States Patent
Dermel et al.

(10) Patent No.: US 11,020,554 B2
(45) Date of Patent: Jun. 1, 2021

(54) ARTIFICIAL VENTILATION APPARATUS WITH VENTILATION MODES SUITED TO CARDIAC MASSAGE

(71) Applicant: Air Liquide Medical Systems, Antony (FR)

(72) Inventors: Marius Dermel, Paris (FR); Eric Jacquot, Antony (FR); Thomas Pennors, Antony (FR); Marceau Rigollot, Montrouge (FR); Jean-Christophe Richard, Antony (FR)

(73) Assignee: Air Liquide Medical Systems, Antony (FR)

( * ) Notice: Subject to any disclaimer, the term of this patent is extended or adjusted under 35 U.S.C. 154(b) by 843 days.

(21) Appl. No.: 15/525,489

(22) PCT Filed: Apr. 6, 2016

(86) PCT No.: PCT/FR2016/050788
§ 371 (c)(1),
(2) Date: May 9, 2017

(87) PCT Pub. No.: WO2016/174324
PCT Pub. Date: Nov. 3, 2016

(65) Prior Publication Data
US 2017/0368280 A1    Dec. 28, 2017

(30) Foreign Application Priority Data
Apr. 28, 2015 (FR) ...................................... 1553809

(51) Int. Cl.
*A61M 16/00* (2006.01)
*A61M 16/20* (2006.01)
(Continued)

(52) U.S. Cl.
CPC ........... *A61M 16/024* (2017.08); *A61B 5/087* (2013.01); *A61H 31/005* (2013.01);
(Continued)

(58) Field of Classification Search
CPC ............ A61B 5/087; A61H 2201/0184; A61H 2201/1619; A61H 2201/5007;
(Continued)

(56) References Cited

U.S. PATENT DOCUMENTS 6,155,257 A * 12/2000 Lurie et al. ......... A61M 31/005
128/204.23
9,180,266 B1 * 11/2015 Sherman ........... A61M 16/0003
(Continued)

FOREIGN PATENT DOCUMENTS

EP    2 198 823    6/2010
EP    2 343 097    7/2011
(Continued)

OTHER PUBLICATIONS

Written Opinion for corresponding PCT/FR2016/050788, dated Aug. 1, 2016.
(Continued)

*Primary Examiner* — Valerie L Woodward
(74) *Attorney, Agent, or Firm* — Allen E. White

(57) ABSTRACT

Disclosed is a method of controlling a respiratory assistance apparatus delivering a flow of gas, particularly a flow of air, having the steps of measuring at least one parameter indicative of the flow of gas; converting at least one parameter indicative of the flow of gas into at least one signal indicative of the flow of gas; processing at least one signal indicative of the flow of gas in order therefrom to deduce at least one item of information relating to cardiac massage being performed on a patient in cardiac arrest; on the basis of at least one deduced item of information, automatically (Continued)

selecting a given ventilation mode from among a number of stored ventilation modes, and controlling the respiratory assistance apparatus by applying the selected ventilation mode. Respiratory assistance apparatus capable of implementing this control method.

13 Claims, 6 Drawing Sheets

(51) Int. Cl.
  *G09B 23/28* (2006.01)
  *A61H 31/00* (2006.01)
  *A61B 5/087* (2006.01)

(52) U.S. Cl.
  CPC ....... *A61H 31/007* (2013.01); *A61M 16/0051* (2013.01); *A61M 16/0069* (2014.02); *A61M 16/201* (2014.02); *G09B 23/288* (2013.01); A61H 2201/0184 (2013.01); A61H 2201/1619 (2013.01); A61H 2201/5007 (2013.01); A61H 2201/5035 (2013.01); A61H 2201/5043 (2013.01); A61H 2201/5048 (2013.01); A61H 2201/5071 (2013.01); A61H 2230/42 (2013.01); A61M 2016/0027 (2013.01); A61M 2016/0039 (2013.01); A61M 2016/0042 (2013.01); A61M 2205/05 (2013.01); A61M 2205/18 (2013.01); A61M 2205/502 (2013.01); A61M 2205/52 (2013.01); A61M 2209/08 (2013.01); A61M 2230/40 (2013.01)

(58) Field of Classification Search
  CPC .... A61H 2201/5035; A61H 2201/5043; A61H 2201/5048; A61H 2201/5071; A61H 2230/42; A61H 31/005; A61H 31/007; A61M 16/0051; A61M 16/0069; A61M 16/024; A61M 16/201; A61M 2016/0027; A61M 2016/0039; A61M 2016/0042; A61M 2205/05; A61M 2205/18; A61M 2205/502; A61M 2205/52; A61M 2209/08; A61M 2230/40; A61M 2016/18; G09B 23/288

See application file for complete search history.

(56) References Cited

U.S. PATENT DOCUMENTS

| | | | |
|---|---|---|---|
| 2005/0137487 A1* | 6/2005 | Zhu | A61B 5/0031 600/513 |
| 2010/0036266 A1 | 2/2010 | Myklebust et al. | |
| 2014/0166014 A1* | 6/2014 | Berthon-Jones | A61M 16/00 128/204.23 |
| 2014/0296675 A1* | 10/2014 | Freeman | A61B 5/7264 600/361 |
| 2015/0045686 A1* | 2/2015 | Lynn | A61B 7/003 600/531 |
| 2015/0328417 A1 | 11/2015 | Löser et al. | |

FOREIGN PATENT DOCUMENTS

| | | |
|---|---|---|
| FR | 3 000 893 | 7/2014 |
| WO | WO 00 20061 | 4/2000 |
| WO | WO 2014 095962 | 6/2014 |

OTHER PUBLICATIONS

International Search Report and Written Opinion for related PCT/FR2016/051298, dated Aug. 1, 2016.

International Search Report for corresponding PCT/FR2016/050788, dated Aug. 1, 2016.

* cited by examiner

ARTIFICIAL VENTILATION APPARATUS WITH VENTILATION MODES SUITED TO CARDIAC MASSAGE

CROSS REFERENCE TO RELATED APPLICATIONS

This application is a 371 of International PCT Application PCT/FR2016/050788 filed Apr. 6, 2016 which claims priority to French Patent Application No. 1553809 filed Apr. 28, 2015, the entire contents of which are incorporated herein by reference.

BACKGROUND

The invention relates to a method of controlling or operating an artificial ventilation apparatus equipped with a micro-blower generating a gas flow, in particular a flow of air, in order to be able to provide ventilatory assistance, in particular ventilation and monitoring, to help a first-aid worker or any other medical personnel, for example an emergency physician, a firefighter, a nurse or the like, when performing cardiac massage on a person who is in cardiac arrest, and also to an artificial ventilation apparatus of this kind.

It is customary to use an artificial ventilation apparatus, also called a respiratory or ventilatory assistance apparatus, or more simply a medical ventilator, in order to provide respiratory assistance, that is to say artificial ventilation, to a person who is having difficulty breathing alone or is unable to breathe alone.

In particular, it is essential to ventilate a person during a cardiac arrest so as to continue supplying oxygen to the brain and to the rest of the body while the heart has stopped.

However, performing ventilation on a person in cardiac arrest while cardiac massage is being performed on this person is problematic, since this ventilation must not interrupt the chest compressions and/or must not be so great that it has adverse hemodynamic effects.

However, conventional ventilators are not designed for this situation. In particular, they emit alarms and/or malfunction during the chest compressions.

Therefore, in practice, the medical personnel deliver insufflations via a ventilator or a bag valve mask (BVM), sometimes interrupting the chest compressions.

The continuity and regularity of the cardiac massage are factors of efficacy that determine the outlook for the patient in cardiac arrest. It is therefore never recommended to stop cardiac massage, even in order to provide the patient with insufflations of respiratory gas.

In addition, the insufflations delivered manually, via a BVM, or by a conventional ventilator are in most cases too aggressive, especially on account of the large volumes of gas that are administered, leading to a direct and recognized adverse effect on the efficacy of the chest compressions.

For this reason, apparatuses that avoid traditional insufflations, especially CPAP (Continuous Positive Airway Pressure) ventilators, have been proposed with a view to being used in cases of cardiac arrest. However, these apparatuses are not ideal since they are unable to ensure sufficient ventilation of the person in cardiac arrest, and the discontinuation of the compressions causes a discontinuation of all ventilation, which is undesirable.

Furthermore, most apparatuses capable of delivering mechanical ventilation during cardiac massage are unable to ensure this ventilation in an autonomous/automatic manner, whereas this complex clinical situation requires great ease of use. Indeed, these apparatuses sometimes require human intervention during each insufflation, which complicates the work of the medical personnel and sometimes leads to gas being administered at a poorly controlled pressure and/or volume. If, during an insufflation of respiratory gas, the pressure and the volume generated are not correctly controlled, phenomena may arise that are damaging to the patient, for example undesirable gastric insufflation. Therefore, with the traditional apparatuses, it is not possible to easily and safely deliver protective ventilation that does not exceed the recommended volume of gas.

In addition, during the cardiac massage, the compressions of the thoracic cage generate a substantial but insufficient pulmonary ventilation, which has to be supplemented by mechanical ventilation. When the chest compressions are interrupted, after resumption of spontaneous circulatory activity of the patient or after an electric shock, for example, the ventilation decreases abruptly, whereas the oxygen demands of the patient increase. Supplementary ventilation is then required, necessitating complex manipulations in order to change the ventilation mode, so as to be able to overcome this lack of oxygen.

Thereafter, once this change of ventilation has been performed and the patient is suitably ventilated, a renewed cardiac arrest may occur. In this case, the chest compressions resume, and it is then once again necessary to manually modify the regulation of the ventilation device so as to recover the ventilation mode that is most suited to cardiopulmonary resuscitation (CPR).

A patient may therefore experience several arrests during his or her management by the medical team, and the delivery of optimal ventilation requires intervention on the part of the medical team in order to adapt the apparatus each time these arrests occur.

However, in an emergency situation, the time spent on these adaptations is to the detriment of more important operations. For lack of time, these adaptations may be forgotten or neglected, which is unacceptable for obvious reasons of safety.

Generally speaking, most of the mechanical ventilation apparatuses currently used during a cardiac massage do not have a specific mode adapted to this situation. They are simply equipped with inhalation triggers which often activate mistakenly and cause self-triggers and cycles that are damaging to the cardiac blood flowrate brought about by the chest compressions. Moreover, some of them do not afford the possibility of regulating a positive expiratory pressure (PEP), however indispensable this may be.

Finally, numerous acoustic and/or visual alarms with which these traditional apparatuses are equipped also mistakenly activate, for example alarms relating to pressure, volume or frequency, since they are developed for "traditional" applications, and the triggers and the alarms use the pressure signals and flowrate signals measured by the machine, which signals, for their part, are greatly disrupted by the cardiac massage.

FR-A-300893 discloses a respiratory assistance apparatus using a control method comprising measurement of a parameter representative of the gas flow, and the use of this parameter in order to deduce therefrom an item of information relating to a cardiac massage performed on a patient in cardiac arrest and in order to automatically select a given ventilation mode from among several memorized ventilation modes. However, said document does not give any details concerning the ventilation modes to be applied.

Similar apparatuses or methods are described by the documents EP-A-2198823, WO-A-00/20061 and EP-A-2343097.

In view of this, the problem addressed is therefore to make available an artificial ventilation apparatus, that is to say a respiratory assistance apparatus, also called a medical ventilator, and a method of controlling or operating such an artificial ventilation apparatus, for solving all or some of the abovementioned problems and disadvantages, by providing a suitable response in terms of ventilation mode depending on the absence or the presence of chest contractions, that is to say cardiac massage performed on a patient in cardiopulmonary arrest.

Preferably, the apparatus and the method must make it possible to detect the performance of cardiac massage, on the patient in cardiac arrest, without human intervention, that is to say automatically.

Moreover, the apparatus and the method must make it possible to provide a mechanical ventilation adapted to the presence or the absence of the cardiac massage, by taking account of the phases of chest compression and those of chest decompression, with a view to improving the efficacy of the ventilation given to the patient, without triggering inappropriate alarms.

In other words, the method of the invention must make it possible to cover all the steps of cardiopulmonary resuscitation (CPR) without interruption, in particular the cyclical phases of chest compression/decompression, and therefore ultimately to improve the ventilation by avoiding interruptions in ventilation and/or any excessive ventilation.

SUMMARY

The solution of the invention thus concerns a respiratory assistance apparatus, that is to say a medical ventilator, comprising a gas circuit designed to deliver a flow of gas, in particular a flow of air, comprising:
  measuring means which are designed to measure at least one parameter representative of the flow of gas delivered by said gas circuit, and which are configured to convert said at least one parameter representative of said flow of gas into at least one signal representative of said flow of gas,
  signal processing means which are able and designed to process said at least one signal representative of the flow of gas provided by the measuring means and to deduce therefrom at least one item of information relating to the performance or the non-performance of cardiac massage on a patient,
  means for memorizing ventilation modes, configured to memorize several ventilation modes comprising at least:
    i) a first ventilation mode corresponding to performance of cardiac massage and
    ii) a second ventilation mode corresponding to non-performance or discontinuation of cardiac massage, and
  means for selecting a ventilation mode, making it possible to select, that is to say able and designed to select, and apply the first or the second memorized ventilation mode depending on said at least one item of information provided by the signal processing means (8) or by user activation of a regulation and selection means (11), characterized in that:
    a) the means for memorizing ventilation modes are configured to memorize:
      a first ventilation mode comprising given values of a first low pressure (PB1), of a first high pressure (PH1), with PH1>PB1, and of a first frequency (F1), and
      a second ventilation mode comprising given values of a second low pressure (PB2), of a second high pressure (PH2), with PH2>PB2, PB2>PB1 and PH2≥PH1, and of a second frequency (F2), with F2>F1, and
    b) the means for selecting a ventilation mode are designed to effect a switchover from the first ventilation mode to the second ventilation mode, or vice versa, so as to modify the high pressure (PH1, PH2) and/or the low pressure (PB1, PB2) and/or the frequency (F1, F2) in response to a detection, by the signal processing means, of at least one item of information relating to an absence or a discontinuation of chest contractions, or, conversely, a presence of chest contractions.

Depending on the circumstances, the apparatus or medical ventilator of the invention can comprise one or more of the following technical features:
  According to a first embodiment, the values of the first and second low pressure (PB1, PB2) are equal, that is to say PB1=PB2. In this case, the low pressure is not modified and is kept constant at a given fixed value PB, hence PB1=PB2=PB.
  According to a second embodiment, the values of the first and second low pressure (PB1, PB2) are different, that is to say PB1<PB2. In this case, the low pressure is modified depending on the selected ventilation mode.
  The means for selecting a ventilation mode are designed to effect a switchover from the first ventilation mode to the second ventilation mode, or vice versa, so as to additionally modify the low pressure (PB1, PB2) in response to a detection, by the signal processing means, of at least one item of information relating to an absence or a discontinuation of chest contractions, or, conversely, a presence of chest contractions.
  The signal processing means make it possible to detect the patient's attempts at spontaneous respiration, by analysis of the disturbances present on the pressure signals and/or flowrate signals. Once they have been detected, the medical ventilator delivers a ventilation cycle in order to respond thereto, between a low pressure (PB1, PB2) and a high pressure (PH1, PH2). This mechanism of synchronization, between the patient requirements and the ventilation delivered, is usually called a trigger. This mechanism of synchronization is active when the second ventilation mode is applied.
  Conversely, this mechanism of synchronization, or trigger, must be deactivated when the first ventilation mode is activated. The presence of the chest compressions prevents the efficient detection of possible attempts made by the patient at spontaneous respiration. Moreover, in a situation of cardiac arrest, this requirement of spontaneous respiration is physiologically inhibited. Consequently, this mechanism of synchronization, or trigger, must be deactivated when the first ventilation mode is activated.
  The signal processing means are configured to operate continuously and to ensure a detection of chest contractions corresponding to an item of information relating to the performance or non-performance of cardiac massage, and to supply said item of information to the means for selecting a ventilation mode, in such a way that said means for selecting a ventilation mode effect a switchover, that is to say change, from a given ventilation mode to another given ventilation mode depending on the presence or the absence of chest contractions, that is to say a thoracic massage.

The means for selecting a ventilation mode are designed to effect a switchover from the first ventilation mode to the second ventilation mode in response to a detection, by the signal processing means, of at least one item of information relating to an absence or a discontinuation of chest contractions.

Conversely, the means for selecting a ventilation mode are designed to effect a switchover from the second ventilation mode to the first ventilation mode in response to a detection, by the signal processing means, of at least one item of information relating to an existence or presence of chest contractions.

Optionally, the means for memorizing ventilation modes are configured to memorize a first ventilation mode additionally comprising a given value of a first oxygen concentration ($FiO_2$-1) and a second ventilation mode comprising a given value of a second oxygen concentration ($FiO_2$-2), and the means for selecting a ventilation mode are designed to effect a switchover from the first ventilation mode to the second ventilation mode so as to additionally modify the oxygen concentration ($FiO_2$-1, $FiO_2$-2) in response to a detection, by the signal processing means, of at least one item of information relating to an absence or a discontinuation of chest contractions.

The means for memorizing ventilation modes are configured to memorize a first ventilation mode that does not comprise a means of synchronization between the ventilation cycles and the patient requirements, and a second ventilation mode that comprises one or more means of synchronization between the ventilation cycles and the patient requirements, and the means for selecting a ventilation mode are designed to effect a switchover from the first ventilation mode to the second ventilation mode so as to activate the one or more means of synchronization between the ventilation cycles and the patient requirements, in response to a detection, by the signal processing means, of at least one item of information relating to an absence or a discontinuation of chest contractions.

The means for memorizing ventilation modes are configured to memorize a first ventilation mode comprising values of a first low pressure (PB1) of between 0 and 20 cm of water, of a first high pressure (PH1) of between 10 and 60 cm of water, with PH1>PB1, and of a first frequency (F1) of between 5 and 40 c/min.

The means for memorizing ventilation modes are configured to memorize a second ventilation mode comprising values of a second low pressure (PB2) of between 0 and 20 cm of water, of a second high pressure (PH2) of between 10 and 60 cm of water, with PH2>PB2, PB2≥PB1 and PH2≥PH1, that is to say depending on the circumstances PB1=PB2=PB or PB1<PB2, and of a second frequency (F2) of between 5 and 40 c/min, with F2>F1.

The means for selecting a ventilation mode make it possible to select and apply the first or the second memorized ventilation mode automatically, depending on said at least one item of information supplied by the signal processing means. In this case, the first or the second ventilation mode is selected automatically by the apparatus depending on the item (or items) of information supplied by the signal processing means. There is therefore no human intervention in this embodiment.

According to another embodiment, the means for selecting a ventilation mode make it possible to select and apply the first or the second memorized ventilation mode in response to the activation, by the user, of a ventilation mode selector, for example one or more buttons, a key or similar, in particular one or more keys situated on a touch screen, that is to say on a man-machine interface. In this case, it is the user activation of the ventilation mode selector that will authorize a selection and an application of the first or the second memorized ventilation mode by the means for selecting a ventilation mode. By way of example, the apparatus is able to propose a ventilation mode to the user, and the latter may or may not validate this by acting on a key or similar.

The means for selecting a ventilation mode are configured to operate according to the first ventilation mode in the case of a detection of the presence of chest contractions.

The measuring means comprise at least one sensor.

The signal processing means comprise at least one electronic board.

The signal processing means comprise at least one microprocessor.

The signal processing means comprise at least one (micro)controller using one or more algorithms.

The means for selecting a ventilation mode comprise regulation or selection means, for example push buttons or rotary knobs, slides, activation or selection keys, or similar, allowing the medical personnel to interact with the ventilator, i.e. to control it, and modify the parameters of the ventilation that is delivered.

The means for memorizing ventilation modes comprise at least one data storage memory, in particular a flash memory or similar.

A motorized micro-blower delivers a respiratory gas, typically air or oxygen-enriched air.

It comprises a gas circuit for conveying the respiratory gas which is delivered by the micro-blower and which is intended to be administered to a patient who is in cardiac arrest.

The micro-blower is operated/controlled by control means.

The motorized micro-blower, also called a turbine, is equipped with an electric motor.

At least part of the gas circuit, the control means and the signal processing means are situated in a rigid shell, that is to say an external envelope forming the cowling of the apparatus.

The gas circuit comprises an internal portion arranged in the rigid shell, and an external portion situated outside the rigid shell.

The internal portion of the gas circuit comprises a gas conduit.

The internal portion of the gas circuit is in fluidic communication with a gas source, so as to be supplied with gas delivered by said gas.

The measuring means are arranged on the external portion of the gas circuit situated outside the rigid shell, so as to perform measurements within said external portion.

The measuring means are arranged on the internal portion of the gas circuit situated within the rigid shell, so as to perform measurements within said internal portion.

It comprises several measuring means, some of which are arranged on the internal portion of the gas circuit, others on the external portion of the gas circuit.

The measuring means comprise sensors.

It additionally comprises a man-machine interface which is able, that is to say designed, to display items of information including at least one item of information relating to the performance of a cardiac massage on the patient who is in cardiac arrest.

The man-machine interface comprises an information display and/or viewing screen, for example a digital screen, in particular a touch screen.

The external portion of the gas circuit is in fluidic communication with a respiratory interface, in particular a breathing mask.

The external portion of the gas circuit comprises a flexible tube or conduit.

The gas source is a source of air (ca. 21% by volume of $O_2$) or of oxygen-enriched air (ca. >21% by volume of $O_2$, typically >50% by volume).

The shell comprises at least one carrying handle to facilitate the transport of the apparatus by a user.

The shell comprises at least one securing device allowing the ventilation apparatus to be secured on a support, for example a bar inside an emergency vehicle, or a rung of a bed or stretcher.

It comprises means for supply of electric current, for example one or more batteries or similar, or one or more cables and one or more connections to the mains supply.

It additionally has regulation and selection means, for example a push button, an activation key, a slide or similar, allowing the medical personnel to act on the ventilator, for example in order to inform the ventilator of the performance of a cardiac massage, to confirm, for the ventilator, a detection of a cardiac massage, to inform the ventilator of the type of respiratory interface used (mask, intubation tube, etc.), to modify one or more mechanical ventilation parameters that are proposed automatically by the ventilator, or for other purposes.

It comprises control means including the signal processing means.

It comprises a micro-blower in fluidic communication with the inhalation branch of the gas circuit, so as to supply the latter with gas delivered by said micro-blower, and the control means are configured to control said micro-blower in such a way as to adjust the pressure or the frequency of the delivered gas, typically air possibly enriched with oxygen.

According to another embodiment, it comprises a first controlled valve arranged on said gas circuit, in particular on the inhalation branch of said circuit, making it possible to regulate the circulation of gas supplying said circuit, said gas originating from an external duct connected to the apparatus, and the control means are configured to control said first controlled valve in such a way as to adjust the pressure or the frequency of the delivered gas, typically air possibly enriched with oxygen.

The invention further relates to a method of controlling, that is to say of operating, a respiratory assistance apparatus delivering a flow of gas, in particular a flow of air, in particular the above-described apparatus according to the invention, said method comprising the steps of:

a) measuring at least one parameter representative of said flow of gas, b) converting said at least one parameter representative of said flow of gas into at least one signal representative of said flow of gas, processing said at least one signal representative of the flow of gas in order to deduce therefrom at least one item of information relating to a cardiac massage performed on a patient who is in cardiac arrest, d) selecting a given ventilation mode from among several memorized ventilation modes, and e) controlling the respiratory assistance apparatus by applying the ventilation mode selected at step d).

According to the control method of the invention:

several ventilation modes are memorized, comprising:
i) a first ventilation mode, called ventilation with cardiac massage, comprising given values of a first low pressure (PB1), of a first high pressure (PH1), with PH1>PB1, and of a first frequency (F1), and optionally of a given first oxygen concentration ($FiO_2$-1), and
ii) a second ventilation mode, called traditional or normal ventilation, that is to say ventilation in the absence of cardiac massage, comprising given values of a second low pressure (PB2), of a second high pressure (PH2), with PH2>PB2, and PH2≥PH1, and of a second frequency (F2), and optionally of a given second oxygen concentration ($FiO_2$-2).

a switchover is effected from the first ventilation mode to the second ventilation mode, or vice versa, so as to modify the high pressure (PH1, PH2) and/or the frequency (F1, F2) in response to a detection, by the signal processing means, of at least one item of information relating to an absence or a discontinuation of chest contractions, or, conversely, a presence of chest contractions.

Depending on the circumstances, the control method of the invention can comprise one or more of the following technical features:

According to a first embodiment, the values of the first and second low pressure (PB1, PB2) are equal, that is to say PB1=PB2. In this case, the low pressure is not modified and is kept constant at a given fixed value PB.

According to a second embodiment, the values of the first and second low pressure (PB1, PB2) are different, that is to say PB1<PB2. In this case, the low pressure is modified depending on the selected ventilation mode.

A switchover is effected from the first ventilation mode to the second ventilation mode, or vice versa, so as to additionally modify the low pressure (PB1, PB2) in response to a detection, by the signal processing means, of at least one item of information relating to an absence or a discontinuation of chest contractions, or, conversely, a presence of chest contractions.

At step c), a detection of chest contractions is performed, and the detection is preferably performed continuously.

At step c), a detection of chest contractions is performed comprising an alternation between phases of compression and relaxation/decompression of the thoracic cage.

The flow of gas is delivered by a micro-blower, with which the respiratory assistance apparatus is equipped, or originates from a gas supply duct connected to the respiratory assistance apparatus, in particular a gas supply duct supplying a wall socket, which is itself fluidically connected to the respiratory assistance apparatus implementing the method of the invention.

The parameter representative of the flow of gas is chosen from among a pressure of the gas, a flowrate of gas insufflated to the patient, a flowrate of gas exhaled by the patient, and a speed of the micro-blower.

When, at step c), an absence or a discontinuation of chest contractions is detected, a switchover is then effected from the first ventilation mode to the second ventilation mode so as to modify the high pressure, the frequency and/or the oxygen concentration, in order to take account of the absence of chest contractions.

When, at step c), at least one item of information relating to a presence or resumption of chest contractions is detected, a switchover is then effected from the second ventilation mode to the first ventilation mode so as to modify the high pressure, the frequency and/or the oxygen concentration, in order to take account of the existence or the presence of chest contractions.

Several alarm algorithms are memorized comprising:

A first set of algorithms, for monitoring with cardiac massage, which are configured to monitor one or more ventilation parameters and/or technical elements of the ventilation apparatus. These algorithms are specific to the conditions encountered during a cardiac massage.

A second set of algorithms, for traditional monitoring, which are configured to monitor one or more ventilation parameters and/or technical elements of the apparatus. These algorithms are adapted to traditional ventilation and can be shared with other ventilation modes that are present.

When, at step c), an absence or a discontinuation of chest contractions is detected, a switchover is then effected from the first set of monitoring algorithms to the second set of monitoring algorithms, so as to adapt the monitoring criteria to the absence of cardiac massage.

When, at step c), at least one item of information relating to a presence or resumption of chest contractions is detected, a switchover is then effected from the second set of monitoring algorithms to the first set of monitoring algorithms, so as to adapt the monitoring criteria to the presence of a cardiac massage.

It comprises a step of displaying the selected ventilation mode.

The motorized micro-blower is controlled in such a way as to maintain a constant minute ventilation in response to a measurement of a volume of gas exchanged between the patient and the respiratory assistance apparatus, regardless of whether a cardiac massage is performed or not.

The motorized micro-blower is controlled in such a way as to deliver gas alternately at a given low pressure (PB1) and at a given high pressure (PH1), with PH1>PB1, in case of detection of cardiac massage.

The motorized micro-blower is controlled in such a way as to increase the high ventilation pressure in response to a detection of a discontinuation of the cardiac massage or of an absence of cardiac massage.

The motorized micro-blower is controlled in such a way as to reduce the high ventilation pressure in response to a detection of performance of a cardiac massage, for example upon a resumption of cardiac massage after a phase of discontinuation of the cardiac massage.

The motorized micro-blower is controlled in such a way as to increase the ventilation frequency (F) in response to a detection of a discontinuation of the cardiac massage.

The motorized micro-blower is controlled in such a way as to reduce the ventilation frequency (F) in response to a detection of performance of a cardiac massage.

The motorized micro-blower is controlled in such a way as to increase the high ventilation pressure (PH2) in response to an action by the user indicative of the change from a ventilation mode with the mask to a ventilation mode with intubation, that is to say the pressure of the gas delivered by the micro-blower is increased when the patient is intubated.

The action by the user, typically the medical personnel, indicative of the change from a ventilation mode with the mask to a ventilation mode with intubation is an activation of a control device such as a key, a push button or the like, said control device activatable by the user being situated on the ventilation apparatus.

The motorized micro-blower is controlled to deliver gas between a first low pressure level (PB1) and a first high pressure level (PH1), with PH1>PB1, in response to an action by the user indicative of a commencement of cardiac massage.

The motorized micro-blower is controlled in such a way as to increase the pressure of the gas delivered by the micro-blower from the first high pressure level (PH1) until it reaches a second high pressure level (PH2), with PH2>PH1>PB1, in response to an action by the user indicative of the discontinuation of the cardiac massage. Optionally, the low pressure of the gas is additionally increased from a value PB1 to a value PB2, with PB2>PB1, and/or the ventilation frequency is increased from a value F1 to a value F2, with F2>F1.

According to another embodiment, the motorized micro-blower is controlled to deliver gas between a first low pressure level (PB1) and a first high pressure level (PH1), with PH1>PB1, in response to an automatic detection, by the apparatus, of a commencement or of the existence of a cardiac massage. Similarly, the motorized micro-blower is controlled in such a way as to increase the pressure of the gas delivered by the micro-blower from the first high pressure level (PH1) until it reaches a second high pressure level (PH2), with PH2>PH1>PB, in response to an automatic detection, by the apparatus, of the discontinuation or of an absence of cardiac massage. Optionally, the low pressure of the gas is also automatically increased from a value PB1 to a value PB2, with PB2>PB1, and/or the ventilation frequency is increased from a value F1 to a value F2, with F2>F1.

The first high pressure level (PH1), the second high pressure level (PH2) and the one or more low pressure levels (PB; PB1, PB2) are memorized.

The first high pressure level (PH1), the second high pressure level (PH2) and the one or more low pressure levels (PB; PB1, PB2) are adjustable by the user.

Generally, according to the invention, the motorized micro-blower is controlled so as to:

i) increase the maximum pressure of the gas delivered by the micro-blower in response to a discontinuation or an absence of cardiac massage, the pressure level preferably being increased as far as the second high pressure level (PH2), the patient then being ventilated between a given low pressure and a high pressure (PH2); and/or ii) reduce the maximum pressure of the gas delivered by the micro-blower in response to a commencement or an existence of cardiac massage, the pressure level preferably being reduced as far as the first high pressure level (PH1), the patient then being ventilated between a given low pressure and a high pressure (PH2).

By way of example, the first low pressure level (PB1) is between about 3 and 15 cm of water, the first high pressure level (PH1) is between about 10 and 40 cm of water, the second high pressure level (PH2) is between about 12 and 60 cm of water, and the second low pressure level (PB2) is between about 3 and 15 cm of water.

Preferably, the low pressure is constant and (PB1=PB2=PB) is of the order of 5 cm of water.

Preferably, the first high pressure level (PH1) is of the order of 15 cm of water, and the second high pressure level (PH2) is of the order of 20 cm of water.

By way of example, the first ventilation frequency (F1) is between about 5 and 40 c/min, and the second ventilation frequency (F2) is between about 10 and 40 c/min.

Preferably, the first ventilation frequency (F1) is of the order of 10 c/min, and the second ventilation frequency (F2) is of the order of 15 c/min.

The micro-blower is controlled by control means, in particular an electronic board, for example with microcontroller and algorithm(s).

Generally speaking, as regards the ventilation mode specific to cardiopulmonary resuscitation, this can be a volumetric or barometric mode, preferably associated with a minimal low pressure (PB) of ventilation, for example of the order of 5 cm $H_2O$.

Advantageously, it is a barometric mode that ensures alternating regulation at several pressure levels, comprising a single low pressure level (PB=PB1=PB2) and one or more high pressure levels (PH1, PH2), with PH2>PH1>PB, for example a low pressure (PB) of the order of 5 cm $H_2O$, and a first high pressure (PH1) of the order of 15 cm $H_2O$, and a second high pressure (PH2) of the order of 20 cm $H_2O$.

The ventilation mode specific to cardiopulmonary resuscitation is able to ensure ventilation of a patient from the start to the end of the intervention in an environment requiring little or no human intervention during the various phases.

In addition to this ventilation mode specific to cardiopulmonary resuscitation, the respiratory assistance apparatus of the invention has other modes of conventional ventilation, for example one or more modes of volumetric ventilation (VAC), barometric ventilation (VPC, VSAI, CPAP, Duo-Levels, etc.) and/or intermittent ventilation (VACI, PVACI, etc.).

In other words, the apparatus according to the present invention makes it possible to cover the various steps of a cardiac massage, that is to say the phases with and without chest compressions, by permitting identification by measuring the variation in pressure and/or in gas flowrate in the airways of the patient, and then a switchover, preferably an automatic switchover, from the ventilation adapted to the chest compressions to the ventilation adapted to the absence of chest compressions, for example after a spontaneous resumption of circulatory activity.

Generally speaking, the signal processing means, in particular an electronic board, for example of the type with microcontroller and algorithm(s), of the apparatus usable within the scope of the invention are able and designed, for example configured or programmed, to select a given prerecorded, i.e. memorized, ventilation mode, which is specific to cardiopulmonary resuscitation, from several memorized ventilation modes, in response to a detection of the performance or the non-performance of a cardiac massage on the patient, that is to say the detection or non-detection of chest compressions by the ventilator itself.

The ventilator thus permits automatic adaptation of the regulation of the ventilation mode, and automatic selection of a specific mode to be used in the context of cardiopulmonary resuscitation.

In particular, it makes it possible to maintain a constant minute ventilation in the absence and in the presence of a cardiac massage, irrespective of the mode of delivery of the cardiac massage. For example, this is done by measurement, by the signal processing means, of the volume of gas exchanged between the patient and the respiratory assistance apparatus.

The selection of a specific ventilation mode to be used in the context of cardiopulmonary resuscitation brings about a modification of the parameters of the mechanical ventilation provided to the patient, in particular the pressures delivered (low pressure and high pressure), the ventilation frequency, the duration for which the low pressure is maintained, the duration for which the high pressure is maintained, the gradient of the pressure increase, the volume delivered for the insufflation, the nature of the gas delivered, etc.

It will be noted that, within the scope of the present invention, the term "means" is regarded as being strictly equivalent to the term "device". Hence, "measuring means" is equivalent to "measuring device"; "display means" is equivalent to "display device"; "processing means" is equivalent to "processing device"; "data storage means" is equivalent to "data storage device", etc.

The invention finally relates to a method for therapeutic treatment of a person in cardiac arrest, in which method a ventilation apparatus according to the present invention is used, and/or a method of controlling or operating such an artificial ventilation apparatus equipped with a micro-blower generating a gas flow, in particular a flow of air, in order to allow ventilatory assistance to be provided to help a first-aid worker or any other medical personnel, for example an emergency physician, a firefighter, a nurse or similar, when they are performing cardiac massage on a person who is in cardiac arrest.

BRIEF DESCRIPTION OF THE DRAWINGS

The present invention will now be described in more detail with reference to the attached figures, in which.

DESCRIPTION OF PREFERRED EMBODIMENTS

Figure 1A:
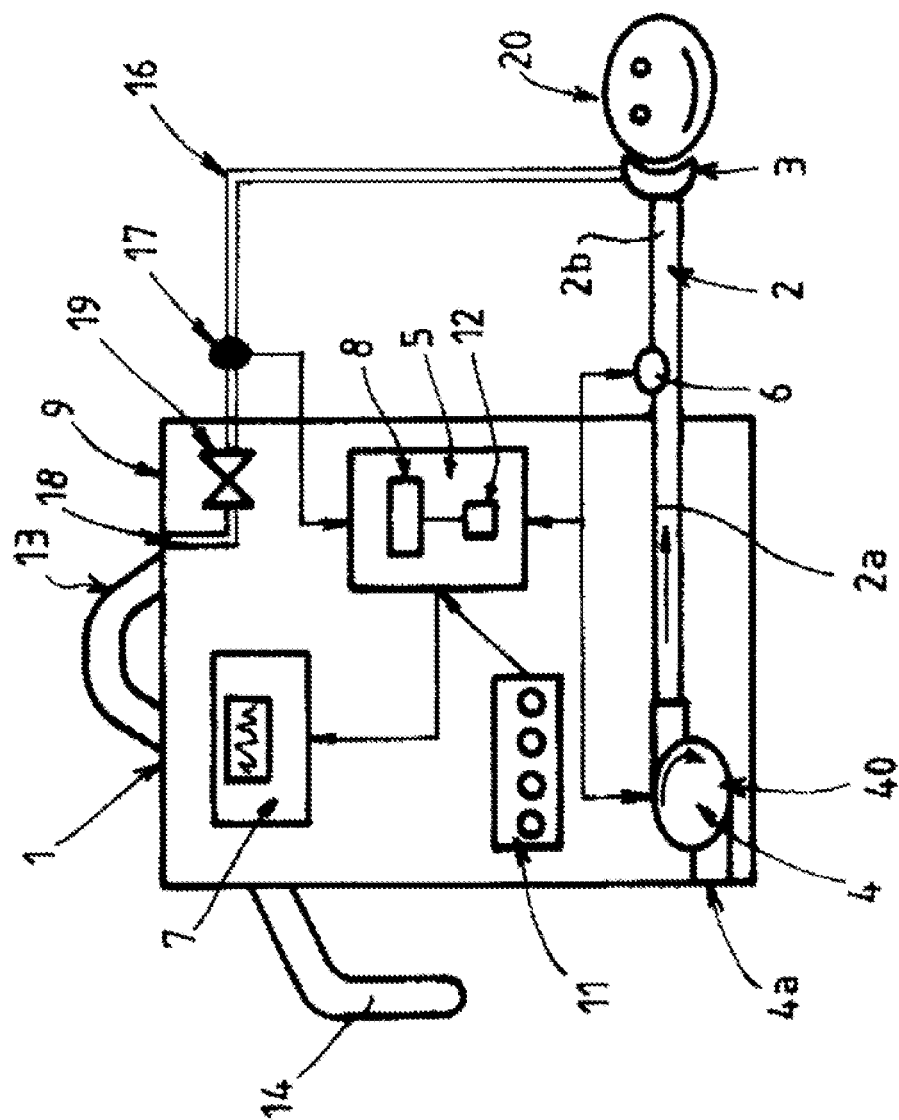
FIGS. 1A and 1B show two embodiments of a respiratory assistance apparatus that can be used to implement the control method according to the present invention.
Figure 1B:
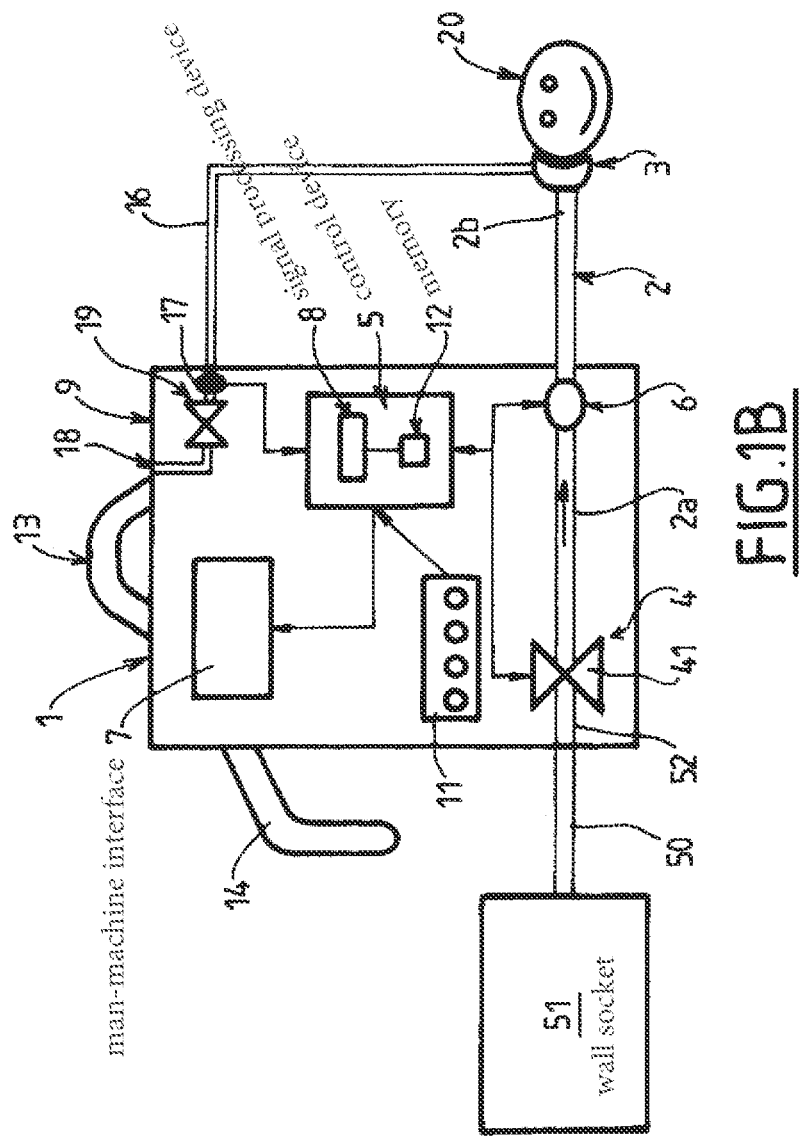

FIGS. 1A and 1B are diagrammatic representations of two embodiments of a ventilatory assistance apparatus or medical ventilator 1 that is suitable for implementing the control method according to the present invention.

The ventilator 1 of FIGS. 1A and 1B comprises a gas source 4, which is a motorized micro-blower 40 in the embodiment of FIG. 1A, also called a turbine, delivering a flow of respiratory assistance gas, typically a flow of air or of oxygen-enriched air, or a controlled valve 41 supplied with gas, via an internal conduit 52, itself in fluidic communication with a gas reservoir or a wall socket 51 for gas supply connected to a network of gas ducts, by way of a flexible conduit 50 connecting the gas reservoir or the wall socket 51 to the internal conduit 52, in the embodiment of FIG. 1B.

In all cases, a ventilatory circuit 2, 16, also called the patient circuit, comprising one or more passages, conduits or gas lines, makes it possible to fluidically connect the gas source 4 of the ventilator 1 to the airways of a patient 20, by way of a patient interface 3, for example a breathing mask or an intubation tube.

The ventilatory circuit 2, 16 comprises at least one inhalation branch 2 for conveying the respiratory gas to the patient 20. It can also comprise an exhalation branch 16 designed to collect the gases exhaled by the patient 20, which are rich in $CO_2$, as is illustrated in FIGS. 1A and 1B. The exhalation branch 16 comprises an exhalation flowrate sensor 17, for example a hot-wire sensor, connected electrically to the signal processing and control means 5, 8, and also an exhalation valve 19 controlled by the control means 5. At its downstream end, the exhalation branch 16 communicates with the atmosphere via a gas outlet orifice 18, while its upstream end is connected to the inhalation branch 2, via a Y-shaped piece, or directly to the patient interface 3.

Measuring means 6 such as a sensor are provided which are able and designed to measure at least one parameter representative of the gas flow, chosen from among the pressure of the gas, the flowrate of gas insufflated by the respirator, the flowrate of gas exhaled by the patient 20, and the speed of rotation of the micro-blower 40, and to deliver at least one signal representative of said at least one measured parameter.

For example, the parameter representative of the flow of gas is the pressure of the gas in the inhalation branch 2 of the ventilatory gas circuit 2, 16, and the measuring means 6 comprise a pressure sensor, of which the pressure tapping is designed in such a way as to permit a measurement of the gas pressure prevailing in said inhalation branch 2 of the ventilatory circuit 2. In the embodiment illustrated in FIGS. 1A and 1B, the pressure tapping serving as measuring means 6 is arranged outside the ventilator. However, according to another embodiment, it may also be located within the ventilator 1.

When the one or more parameters representative of the flow of gas have been measured, this measured parameter is converted into at least one signal representative of the flow of gas, which is then transmitted to and analyzed by signal processing means 8, in order to deduce therefrom at least one item of information relating to a cardiac massage performed on a patient in cardiac arrest.

The signal processing means 8 form part of the control means 5 of the ventilator 1 and comprise one or more electronic boards.

The one or more signals are transmitted by the measuring means 6 to the signal processing means 8 via a suitable link, that is to say electrical links such as cables or the like.

Thereafter, the signal processing means 8 are able to deduce or determine therefrom:
that a cardiac massage is being performed on the patient 20 and whether the phase in progress is a phase of compression or a phase of relaxation of the thoracic cage;
the volume of gas insufflated by the ventilator 1 to the patient 20, in the course of the mechanical ventilation cycles and during the phases of relaxation of the thoracic cage. The volumes of insufflated gas can be added together over a given period of time, for example 1 minute. Of course, the addition can be performed for longer than 1 minute or, conversely, for less than 1 minute;
the volume of gas exhaled by the patient 20, in the course of the mechanical ventilation cycles and during the phases of relaxation of the thoracic cage. Here too, the volumes of exhaled gas can be added together over a given period of time, for example 1 minute; of course, the addition can be performed for longer than 1 minute or, conversely, for less than 1 minute.

In other words, by virtue of the signal processing means 8, a detection of chest contractions is preferably performed, preferably in a continuous manner, that is to say a detection of an alternation of phases of compression and of relaxation/decompression of the thoracic cage.

The signal processing means 8 are thus able and designed:
i) to process the signal corresponding to the parameter representative of the flow of gas and, for example, to detect one or more positive or negative variations greater than one or more threshold values representative of the phases of compression or relaxation of the thoracic cage in the course of a cardiac massage. These threshold values are recorded in a storage memory 12, for example a flash memory. These threshold values can be numerical values, tables of values, curves, etc.
ii) to integrate, on the signal corresponding to the parameter representative of the flow of gas, the gas flowrate generated by the ventilator 1 during the chest compressions and the cycles generated by the machine.
iii) to integrate, with respect to time, the signal corresponding to the parameter representative of the flow of gas, and the gas flowrate generated by the ventilator 1 during the chest compressions and the cycles generated by the ventilator 1.
iv) to integrate, with respect to time, the signal corresponding to the parameter representative of the flow of gas, and the gas flowrate exhaled by the patient 20 during the chest compressions and the cycles generated by the ventilator 1.

To do this, the signal processing means 8 preferably comprise a microprocessor programmed in particular with one or more processing algorithms, as is explained in detail below.

Thereafter, depending on the deduced information concerning cardiac massage, the ventilator 1 performs an automatic selection of a given ventilation mode from among several memorized ventilation modes, and the respiratory assistance apparatus is controlled by applying the ventilation mode that has thus been selected.

The ventilator 1 thus comprises means that are able and designed to automatically adapt, that is to say without human intervention, the parameters of the mechanical ventilation delivered to the patient 20, if the signal processing means 8 detect or do not detect the alternation of compression and relaxation of the thoracic cage, that is to say the presence or absence of a cardiac massage, with the aim of ensuring optimal ventilation of the patient 20.

To put it another way, an automatic switchover from a given ventilation mode to another given ventilation mode is therefore performed depending on a detection or determination of the presence or absence of chest contractions, said ventilation modes being memorized in memorizing means, such as a memory 12.

In particular, it is possible to memorize several ventilation modes comprising a first ventilation mode and a second ventilation mode, which are implemented depending on whether or not a cardiac massage takes place.

In order to simplify the explanations, it is assumed hereinafter that the low pressure PB is kept constant irrespective of the ventilation mode chosen, that is to say PB1=PB2=PB.

However, as has been explained above, the low pressure could also vary between a first low pressure PB1 and a second low pressure PB2, with PB2>PB1. Generally, this therefore gives: PB2≥PB1.

Thus, the first ventilation mode, which comprises given values of a first low pressure PB1, here with PB1=PB, of a first high pressure (PH1), with PH1>PB, of a first frequency (F1) and/or of a first oxygen concentration ($FiO_2$-1), is implemented in the case of detection of thoracic massage.

Conversely, the second ventilation mode, which comprises given values of a second low pressure (PB2), here with PB2=PB1=PB as mentioned above, of a second high pressure (PH2), with PH2>PB and PH2>PH1, of a second frequency (F2) and/or of a second oxygen concentration ($FiO_2$-2), is implemented in the case of detection of an absence of thoracic massage or after discontinuation of thoracic massage, that is to say in the case of absence or discontinuation of chest contractions, for example if the patient's heart starts beating "normally" again.

Indeed, the ventilator 1 then effects an automatic switchover from the first ventilation mode to the second ventilation mode in order to modify the high pressure, the frequency and/or the oxygen concentration. Thus, if at least one item of information is detected relating to a presence or resumption of the chest contractions, an immediate switchover is then performed from the second ventilation mode to the first ventilation mode in order to modify the high pressure, the frequency and/or the oxygen concentration.

Thus, according to a "barometric" ventilation mode, it is possible to implement an alternating regulation of pressure between several pressure levels comprising a low pressure level (PB) and several high pressure levels (PH1, PH2), with PH2>PH1>PB, the first high pressure (PH1) being implemented in the case of detection of cardiac massage, and the second high pressure (PH2) being implemented in the case of non-detection, that is to say absence or discontinuation, of cardiac massage. For example, a low pressure (PB) is of the order of 5 cm $H_2O$, the first high pressure (PH1) is of the order of 15 cm $H_2O$, and the second high pressure (PH2) is of the order of 20 cm $H_2O$.

Similarly, the frequency used can be increased in the case of detection of an absence or discontinuation of the cardiac massage, in such a way as to compensate for the loss of ventilation caused by the discontinuation of the chest compressions. For example, the frequency of ventilation can increase from an initial frequency F1 of the order of 10 cycles/min to a higher frequency F2 of the order of 15 cycles/min. Conversely, the frequency can go from F2 to F1 if the chest compressions are resumed in the case of renewed cardiac arrest.

By analogy, it is also possible to reduce the FiO2 in the case of detection of an absence or discontinuation of the cardiac massage. For example, the FiO2 delivered can be 50%. Conversely, the FiO2 can be increased if the chest compressions are resumed in the case of renewed cardiac arrest, for example from 50% to 100%.

Alternatively or in addition, the ventilator 1 makes it possible to automatically adapt the parameters of the mechanical ventilation delivered to the patient 20 in order to maintain a constant total minute ventilation, on the basis of the measurements effected by the signal processing means 8.

Figure 2:
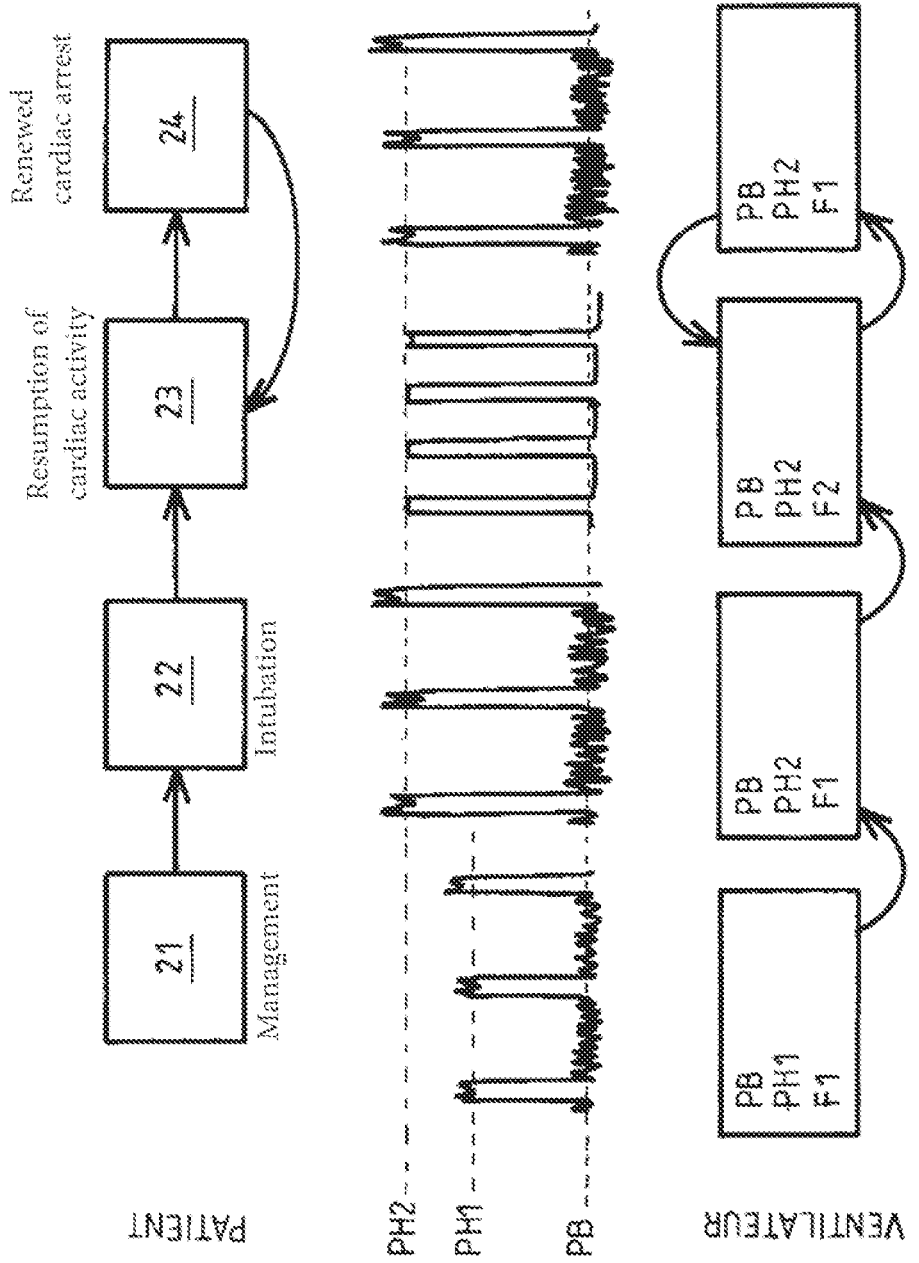
FIG. 2 is a representation of the various steps in the management of a patient and of the adjustments made by the respiratory assistance apparatus implementing the control method according to the present invention.
Figure 3A:
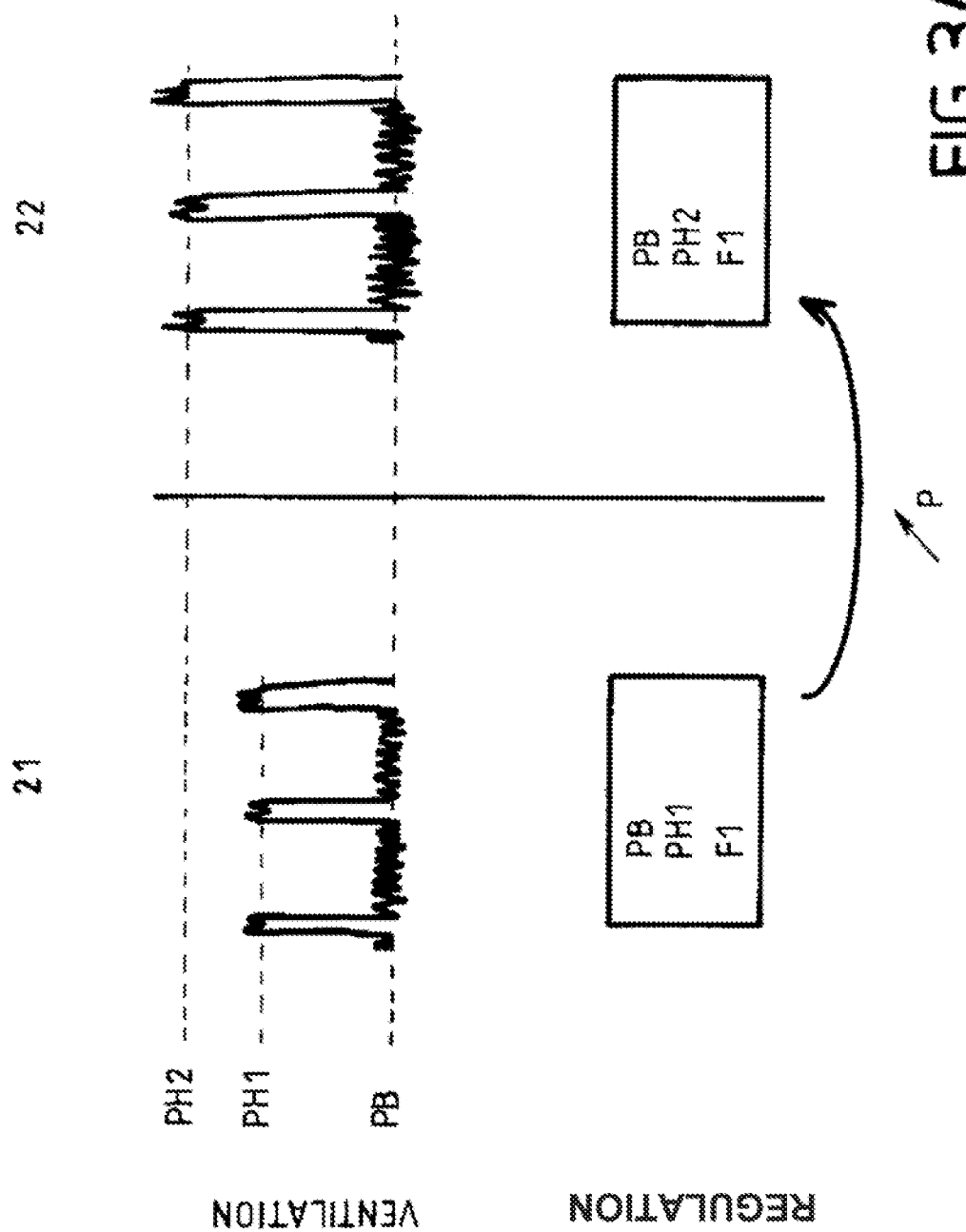
FIGS. 3A to 3C are detailed illustrations of FIG. 2.
Figure 3B:
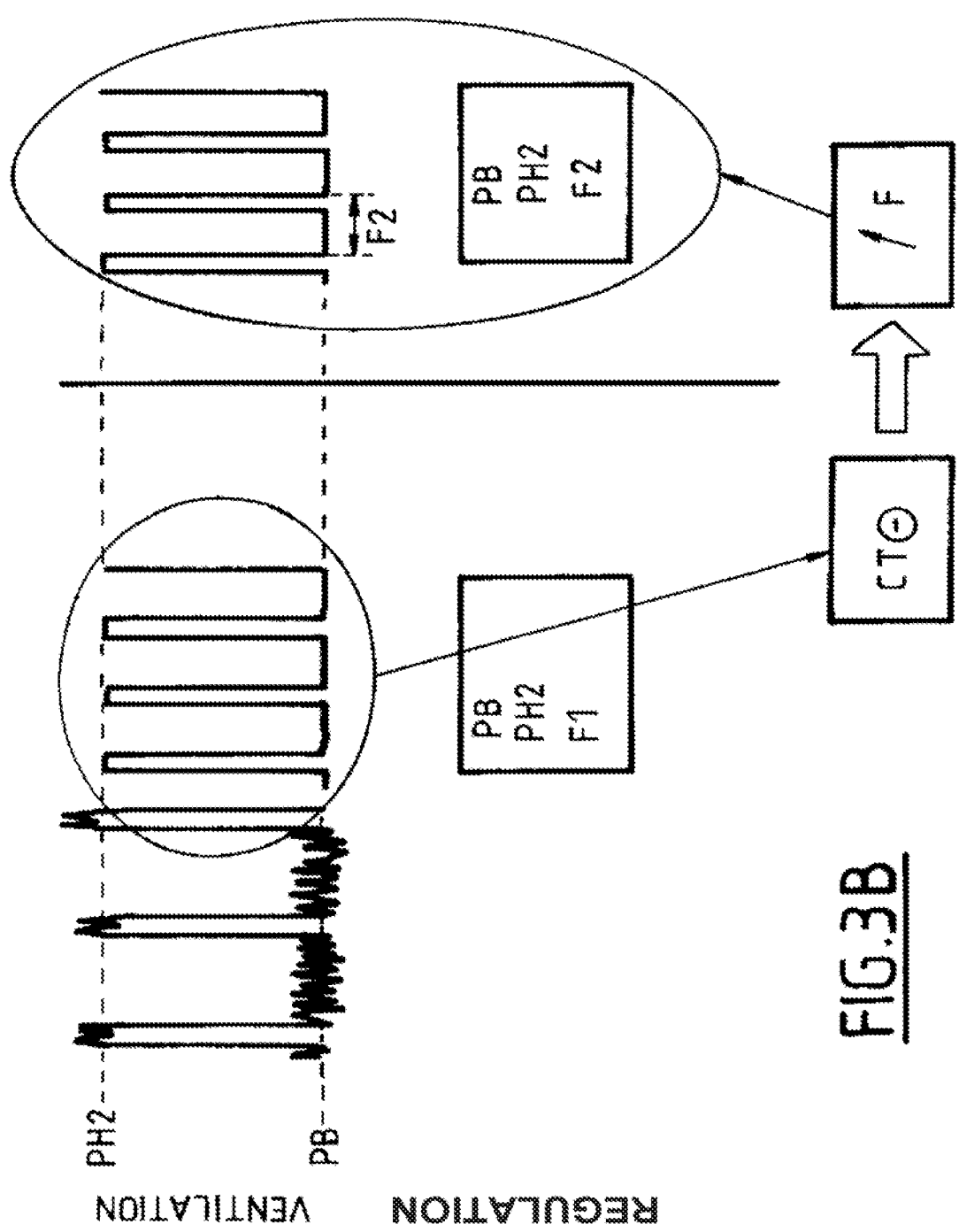
Figure 3C:
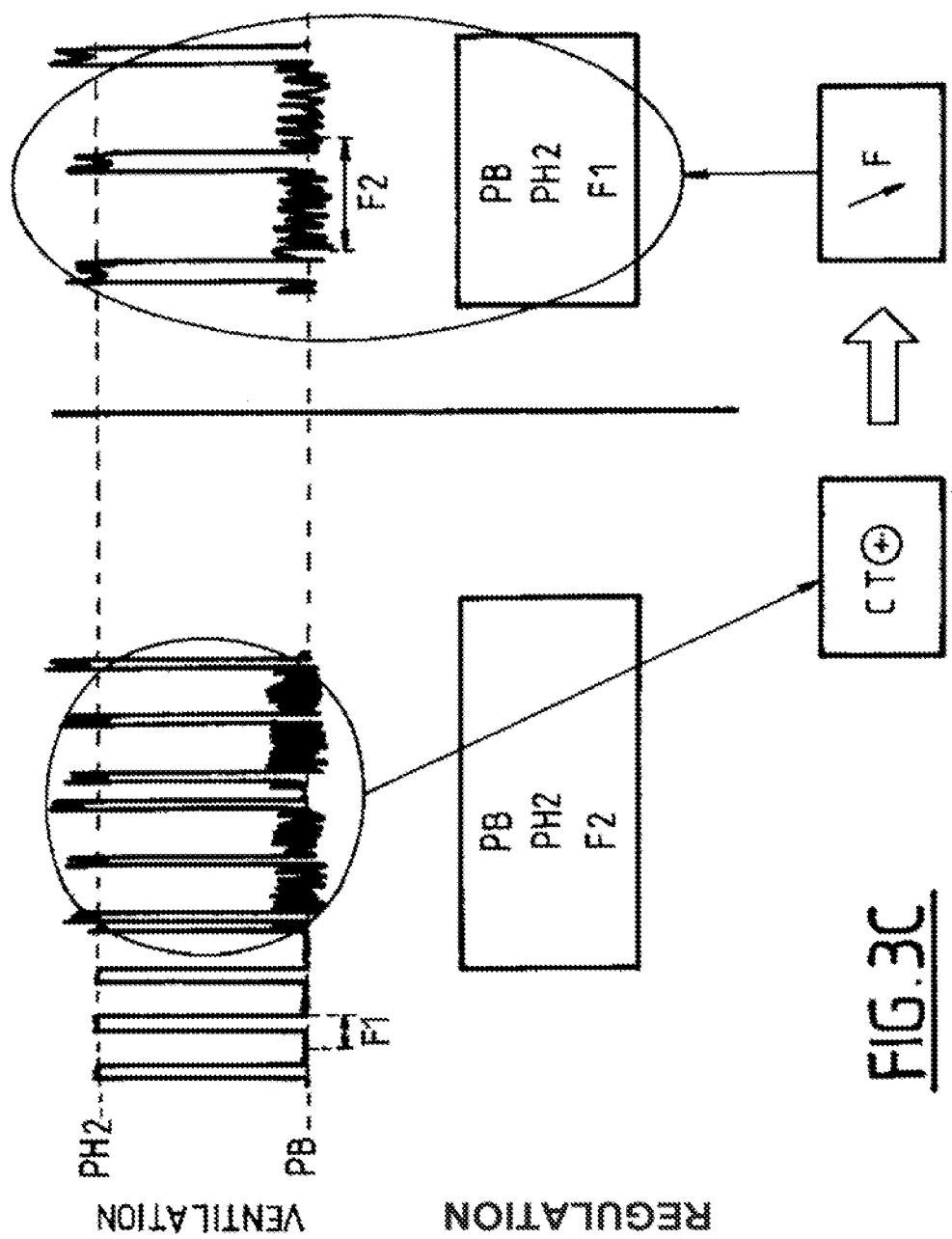

Within the context of a barometric ventilation between several pressure levels, the parameters adapted can be the pressures delivered, in particular the pressure regulated during the low level of ventilation, called low pressure (PB), and the one or more high pressures (PH1, PH2, etc.) regulated during the high level, or else the frequency (F) of ventilation, the duration for which the low pressure is maintained, the duration for which the high pressure is maintained, the gradient of the pressure increase, the volume delivered for the insufflation, the nature of the gas delivered, etc. The adaptation of the pressure levels is illustrated in FIGS. 2 and 3.

Alternatively or in addition, the ventilator 1 can comprise means for changing the alarm algorithms, for example alarms aimed at monitoring the respiratory rhythm of the patient, the pressure delivered by the respirator or the volume delivered by the respirator, which are able and designed to change from a first algorithm to a second algorithm in response to a detection, by the signal processing means, of the performance of a cardiac massage on the patient, so as not to trigger a false alarm, which would needlessly disturb the first-aid worker.

The ventilator 1 and its components, requiring power in order to function, are supplied directly or indirectly with electrical current from one or more rechargeable or non-rechargeable batteries, from the electricity supply of the emergency vehicle that it equips or from the mains supply, hence at a voltage that can be as much as about 230 V. If necessary, it can incorporate a current converter designed to reduce the supply voltage to a use voltage that is of a lower value.

Finally, a man-machine interface 7, such as a displaying and viewing screen, for example a touch screen, makes it possible to display, and thus allows the user to view, items of information relating to the ventilation delivered, such as the pressure and the flowrate measured by the measuring means 6.

Also provided are regulation and selection means 11, for example push buttons or rotary knobs, slides, activation or selection keys or similar, allowing the medical personnel to inform the ventilator 1 of the performance of a cardiac massage and/or to confirm, for the ventilator 1, the detection made of the performance of a cardiac massage, and to inform the ventilator of the type of interface with the patient, for example mask, intubation tube, etc.

These regulation and selection means 11 also make it possible, if need be, to modify the mechanical ventilation parameters that are proposed automatically by the ventilator 1, or, depending on the embodiment in question, to be able to inform the ventilator 1 of a change in the nature of the gas used, for example the move from air to an air/oxygen mixture, or a change in the oxygen content of an air/oxygen mixture.

As can be seen in FIG. 1, at least part of the gas circuit 2, 16, the signal processing means 8 and the gas source 4 are arranged in a cowling or a rigid shell 9 which forms the outer envelope of the apparatus 1. This shell 9 includes or moreover supports other components such as the man-machine interface 7, the one or more memories 12, the regulation and selection means 11, etc.

The inhalation branch 2 of the gas circuit 2, 16 comprises two distinct portions, namely an internal portion 2a arranged in the rigid shell 9, for example a gas conduit, and an external portion 2b situated outside the rigid shell 9 and including, for example, a flexible hose. The internal portion 2a of the inhalation branch 2 is in fluidic communication with the gas source 4, namely the motorized micro-blower 40 in FIG. 1A, having an air intake or inlet 4a communicating with the ambient atmosphere, or the first controlled valve 41 in FIG. 1B, in such a way as to supply said internal portion 2a with air, optionally enriched in oxygen.

The motorized micro-blower 40 (FIG. 1A) or the first controlled valve 41 (FIG. 1B) is controlled by control means 5, preferably an electronic board with microprocessor, such as a microcontroller, using one or more algorithms. Preferably, the control means 5 include the signal processing means 8 and are configured to control the motorized microblower 40 or the first controlled valve 41 as a function of the signals transmitted by the signal processing means 8.

Moreover, the external portion 2b of the inhalation branch 2 of the gas circuit 2, 16 situated outside the rigid shell 9 is for its part in fluidic communication, at the upstream end, with the internal portion 2a of the inhalation branch 2 and, at the downstream end, with the respiratory interface 3, such as a mask or an intubation tube, so as to ensure fluidic continuity between the gas source 4 and the patient 20 and to allow the respiratory gas, e.g. the air arriving from the turbine, to reach the airways of said patient.

In FIGS. 1A and 1B, the measuring means 6, typically one or more sensors, are arranged on the external portion 2b of the inhalation branch 2 situated outside the rigid shell 9, in order to perform the desired measurements, for example of pressure and/or flowrate, within said external portion 2b. Of course, the measuring means 6 can also be arranged inside the shell 9. In all cases, the link between the measuring means 6 and the processing means 8 and/or the control means 5, and hence the transfer of the measurement signals, is effected by wired connections, for example.

Optionally, the shell 9 can also comprise at least one carrying handle 13 to facilitate the transport of the apparatus 1 by the user, as is essential in some emergency situations, and/or a securing device 14 allowing the ventilation apparatus 1 to be secured on a support, for example a bar inside an emergency vehicle, or a rung of a bed or stretcher.

FIGS. 2 and 3A to 3C are schematic representations of the various steps in the procedure of managing a patient and of the adaptations made by the ventilatory assistance apparatus or ventilator 1 using the control method according to the present invention, in particular the regulation of the pressure levels of the gas that is delivered.

More precisely, this procedure comprises the following successive phases:

Phase 21—Management (see FIGS. 2 and 3A): The patient in cardiac arrest is ventilated with the mask, and cardiac massage begins to be applied by the medical personnel. The ventilator 1 then performs mechanical ventilation of the patient in barometric mode, that is to say between several pressure levels, namely an initial pressure value, called "low pressure" or PB, for example 5 cm of water, and a first high pressure value (PH1), also called "intermediate pressure", for example 10 cm of water, with PB<PH1, and at a given ventilation frequency F1, here 10 cycles/min.

Phase 22—Intubation of the patient 20 (see FIGS. 2 and 3A): The medical personnel then informs the ventilator 1 of a change of respiratory interface, such as the move from ventilation with the mask to ventilation by intubation tube, by activating a push button or the like. The cardiac massage is then continued by the medical personnel. The ventilator 1 then automatically adapts the ventilation parameters by increasing the high ventilation pressure, by means of moving it from the first high pressure PH1 to a greater pressure, namely the second high pressure PH2, with PH2>PH1. For example, PH2 is equal to 15 cm of water. The ventilation is then continued between the levels PB and PH2. The frequency F1 is kept constant, i.e. at a frequency F1 of 10 cycles/min.

Phase 23—Resumption of cardiac activity (see FIGS. 2 and 3B): If spontaneous cardiac activity is detected by the medical personnel, the cardiac massage is discontinued. The ventilator 1 then detects the discontinuation of the cardiac massage and automatically adapts the ventilation parameters by increasing the frequency of the mechanical ventilation in order to compensate for the loss of ventilation caused by the discontinuation of the chest compressions (CT (−) in FIG. 3B), for example the ventilation frequency increases to a higher frequency F2, with F2>F1, of the order of 15 cycles/min. The pressure levels are unchanged; the ventilation is continued between the levels PB and PH2.

Phase 24—In the event of renewed cardiac arrest (see FIGS. 2 and 3C): Following the resumption of spontaneous cardiac activity in Phase 23, a renewed cardiac arrest may occur and then requires a resumption of the cardiac massage by the medical personnel and a reappearance of the chest contractions (CT (+) in FIG. 3C). The ventilator 1 then detects this resumption of the cardiac massage and in this case too automatically adapts the ventilatory parameters by reducing the frequency of the mechanical ventilation, for example by reducing it to its initial level F1 of 10 cycles/min, while maintaining the pressure levels PB and PH2 as in Phase 23.

Before obtaining a lasting resumption of spontaneous activity, several cardiac arrests may occur. In this case, the procedure alternates between Phase 23 without cardiac massage and Phase 24 with resumption of cardiac massage (see FIGS. 2 and 3C). The ventilator 1 automatically adapts the mechanical ventilation delivered to the patient by reducing the ventilation frequency from F2 to F1, at each transition from Phase 23 to Phase 24 or, conversely, by increasing the ventilation frequency from F1 to F2 in order to compensate for the loss of ventilation caused by the discontinuation of the chest compressions, at each transition from Phase 24 to Phase 23.

During the transitions between phases 22, 23 and 24, the ventilation frequency is adapted to deliver sufficient ventilation just as would be provided by the parameters PB, PH1, PH2, or else the delivered oxygen concentrations designated FiO2-1 and FiO2-2.

The respiratory assistance apparatus according to the present invention can be used in the context of ventilation of a person who is in cardiac arrest and who is receiving cardiac massage.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A respiratory assistance apparatus (1) comprising a gas circuit (2, 16) designed to deliver a flow of gas comprising:
    a measuring device (6) which is designed to measure at least one parameter representative of the flow of gas delivered by an inhalation branch (2) of said gas circuit (2, 16), and the measuring device is configured to convert said at least one parameter representative of said flow of gas into at least one signal representative of said flow of gas,
    a signal processing device (8) which is able and designed to process said at least one signal representative of the flow of gas provided by the measuring device (6) and to deduce therefrom at least one item of information relating to a performance or to a non-performance of a cardiac massage on a patient,
    a memory device (12) configured to store several ventilation modes comprising at least:
        i) a first ventilation mode corresponding to the performance of the cardiac massage and
        ii) a second ventilation mode corresponding to the non-performance or discontinuation of the cardiac massage, and
    a selection system configured and adapted to select the first or the second stored ventilation mode depending on said at least one item of information provided by the signal processing device (8) or by user activation of a regulation and selection input (11),
    wherein:
    a) the memory device (12) for storing ventilation modes is configured to store:
        the first ventilation mode comprising given values of a first low pressure (PB1), of a first high pressure (PH1), with PH1>PB1, and of a first frequency (F1), and
        the second ventilation mode comprising given values of a second low pressure (PB2), of a second high pressure (PH2), with PH2>PB2 and PH2≥PH1, and of a second frequency (F2), with F2>F1, and
    b) the selection system is designed to effect a switchover from the first ventilation mode to the second ventilation mode, or vice versa, so as to modify the high pressure (PH1, PH2) and the frequency (F1, F2) in response to a detection of the at least one item of information relating to an absence or a discontinuation of a chest contraction, or, conversely, a presence of the chest contraction corresponding to the chest massage.

2. The apparatus as claimed in claim 1, wherein the signal processing device (8) is configured to operate continuously and to ensure an automatic detection of the chest contractions corresponding to the item of information relating to the performance or non-performance of the cardiac massage, and to provide said item of information to the selection system, such that said selection system effects a switchover from a given ventilation mode to another given ventilation mode depending on the presence or the absence of the chest contractions.

3. The apparatus as claimed in claim 2, wherein the selection system is designed to effect:
    a switchover from the first ventilation mode to the second ventilation mode in response to a detection, by the signal processing device (8), of the at least one item of information relating to the absence or the discontinuation of the chest contractions, or
    a switchover from the second ventilation mode to the first ventilation mode in response to a detection, by the signal processing device (8), of the at least one item of information relating to an existence or the presence of the chest contractions.

4. The apparatus as claimed in claim 3, wherein the measuring device (6) comprises at least one sensor and/or the signal processing device (8) comprises a controller using one or more algorithms.

5. The apparatus as claimed in claim 4, wherein the selection system comprises a regulation or a selection device (11) that can be actuated by a user to inform the apparatus (1) of the performance of the cardiac massage, to confirm a detection of the cardiac massage, to indicate a type of respiratory interface used, or to modify one or more mechanical ventilation parameters that are proposed automatically by the apparatus.

6. The apparatus as claimed in one of claim 1, wherein the memory device (12) for storing ventilation modes comprises at least one flash memory.

7. The apparatus as claimed in claim 1, further comprising an information display screen (7).

8. The apparatus as claimed in claim 1, further comprising a control system (5) including the signal processing device (8).

9. The apparatus as claimed in claim 8, wherein:
    the apparatus (1) further comprises a micro-blower (40) in fluidic communication with the inhalation branch (2) of the gas circuit (2, 16), or a first controlled valve (41) arranged on said gas circuit (2, 16),
    and the control system (5) is configured to command said micro-blower (40) or said first valve (41).

10. The apparatus as claimed in claim 1, wherein:
    the memory device (12) is configured to store the first ventilation mode additionally comprising a given value of a first oxygen concentration ($FiO_2$-1) and the second ventilation mode additionally comprising a given value of a second oxygen concentration ($FiO_2$-2), and
    the selection system is designed to effect a switchover from the first ventilation mode to the second ventilation mode so as to additionally modify the oxygen concentration ($FiO_2$-1, $FiO_2$-2) in response to a detection, by the signal processing device (8), of the at least one item of information relating to the absence or the discontinuation of the chest contractions.

11. The apparatus as claimed in claim 1 wherein:
    the memory device (12) is configured to store the first ventilation mode further characterized in that the first ventilation mode does not comprise a synchronization data representing a synchronization between the ventilation cycles and a patient requirement, and store the second ventilation mode that further comprises one or more synchronization data representing a synchronization between the ventilation cycles and the patient requirement, and the selection system is designed to effect a switchover from the first ventilation mode to the second ventilation mode so as to activate one or more synchronization controls configured and adapted to synchronize the ventilation cycles and the patient requirement, in response to a detection, by the signal processing device (8), of the at least one item of information relating to the absence or the discontinuation of the chest contractions.

12. The apparatus as claimed in claim 1, wherein the memory device (12) is configured to store the first ventilation mode comprising values of a first low pressure (PB1) of between 0 and 20 cm of water, of the first high pressure (PH1) of between 10 and 60 cm of water, with PH1>PB1, and of the first frequency (F1) of between 5 and 40 c/min.

13. The apparatus as claimed claim 1, wherein the memory device (12) is configured to store the second ventilation mode comprising values of the second low pressure (PB2) of between 0 and 20 cm of water, of the second high pressure (PH2) of between 10 and 60 cm of water, with PH2>PB2, PB2≥PB1 and PH2≥PH1, and of the second frequency (F2) of between 5 and 40 c/min, with F2>F1.

* * * * *